United States Patent
Gritzky et al.

(10) Patent No.: US 7,376,252 B2
(45) Date of Patent: May 20, 2008

(54) USER INTERACTIVE METHOD AND USER INTERFACE FOR DETECTING A CONTOUR OF AN OBJECT

(75) Inventors: Arthur Gritzky, Pollham (AT); Armin Schoisswohl, Wels (AT)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 770 days.

(21) Appl. No.: 10/722,171

(22) Filed: Nov. 25, 2003

(65) Prior Publication Data
US 2005/0111710 A1 May 26, 2005

(51) Int. Cl.
*G06K 9/00* (2006.01)

(52) U.S. Cl. .................. 382/128; 382/199; 378/21

(58) Field of Classification Search ........ 382/128–134, 382/154, 168, 109, 199, 169, 178, 181, 203, 382/255, 260, 274, 276, 285, 291–294, 318, 382/100, 232, 242, 295, 297, 298, 305, 296; 600/450, 443; 378/21, 29
See application file for complete search history.

(56) References Cited

U.S. PATENT DOCUMENTS

| | | | | |
|---|---|---|---|---|
| 5,148,494 A | * | 9/1992 | Keskes | ........................ 382/109 |
| 5,170,440 A | * | 12/1992 | Cox | ........................... 382/199 |
| 5,566,246 A | * | 10/1996 | Rao | ........................... 382/154 |
| 6,106,466 A | * | 8/2000 | Sheehan et al. | ............. 600/443 |
| 6,346,124 B1 | * | 2/2002 | Geiser et al. | ............... 600/450 |
| 6,482,159 B1 | * | 11/2002 | Wiesauer et al. | ........... 600/443 |
| 6,628,743 B1 | | 9/2003 | Drummond et al. | |
| 6,716,175 B2 | | 4/2004 | Geiser et al. | |
| 6,724,938 B1 | | 4/2004 | Matsumura et al. | |
| 7,110,583 B2 | * | 9/2006 | Yamauchi | .................... 382/128 |

FOREIGN PATENT DOCUMENTS

JP        03269691        3/1998

OTHER PUBLICATIONS

Juvin, Anima (ANalysis of IMAges) A Quasi Real Time System, IEEE 1982, 5 pgs.

* cited by examiner

*Primary Examiner*—Seyed Azarian
(74) *Attorney, Agent, or Firm*—The Small Patent Law Group LLP; Dean D. Small (57) ABSTRACT

Method and apparatus for detecting a contour of an object within an image is provided. A user interface is used to select first and second points within the object. A processor detects first and second subcontours based on the first and second points, respectively; and the first and second subcontours are based on detected edges. The detected edges are representative of non-uniformities within the image. The processor defines subcontours around each of the points, and the subcontours are combined into a contour.

18 Claims, 8 Drawing Sheets

Prior to Step 226    With Contour of Step 226

FIG. 8

Prior to Step 226    With Contour of Step 226

FIG. 13

USER INTERACTIVE METHOD AND USER INTERFACE FOR DETECTING A CONTOUR OF AN OBJECT

BACKGROUND OF THE INVENTION

This invention relates generally to diagnostic ultrasound systems. In particular, the present invention relates to method and apparatus for interactively detecting the contour of an object.

Various algorithms are available which search for the outside edge, or contour of an object, within an image. These algorithms may be used to calculate various size dimensions of the object. For example, the object may be an organ, cyst, or tumor which the user is interested in further analyzing to determine proper treatment.

Problems exist with the current algorithms and user interface methods, however. For example, a user may select a single starting point within an object. The algorithm starts with the single starting point and searches outward looking for changes within the tissue which identify boundaries between different types of tissue. Another method is to employ known shapes, such as circles and ovals, then require the user to drag the contour to the desired location around the object. Still another method has the user draw the contour of the object using a mouse or various keyboard keys, which can be quite time consuming, with accuracy being affected by the display size and resolution, and the minimum distance the user may move the cursor on the display. Also, working with 3D images adds an additional element of complexity.

Additionally, tissue in the body is not uniform. High contrast boundaries exist between different types of tissue, such as bone and muscle, and muscle and blood. Lower contrast boundaries exist also, such as a change within the density of the muscle, organ, or tumor. An automatic searching algorithm may detect a boundary close to the starting point which does not reflect the contour of the object, and thus exclude portions the object. Alternatively, the algorithm may search for a boundary having a greater contrast and include areas which are outside the object.

Thus, a system and method are desired to obtain a contour of an object within an image that addresses the problems noted above and others previously experienced.

BRIEF DESCRIPTION OF THE INVENTION

In one embodiment, an apparatus for detecting a contour of an object within an image comprises a user interface for selecting first and second points within an object which is within an image. A processor detects first and second subcontours based on the first and second points, respectively; and the first and second subcontours are based on detected edges. The processor combines the first and second subcontours into a contour.

In one embodiment, a user interactive method for detecting the contour of an object within an image comprises selecting a first point within an object using a user interface. A first subcontour is identified based on the first point. A second point is selected within the object using the user interface, and a second subcontour is identified based on the second point. A contour is defined based on the first and second subcontours.

In one embodiment, parameters of an object within an image may be calculated and/or measured. An image comprising an object having pixel or Voxel data is acquired. Points are selected within the object by using a user interface. As the points are selected, edges are searched for within the image around the points. The edges are representative of non-uniformities in the pixel or Voxel data and define subcontours around each of the points. The subcontours are combined into a contour as each of the subcontours is defined. Parameters such as area, volume, circumference, long axis, short axis, and longest distance may be calculated within the contour.

DETAILED DESCRIPTION OF THE INVENTION

Figure 1:
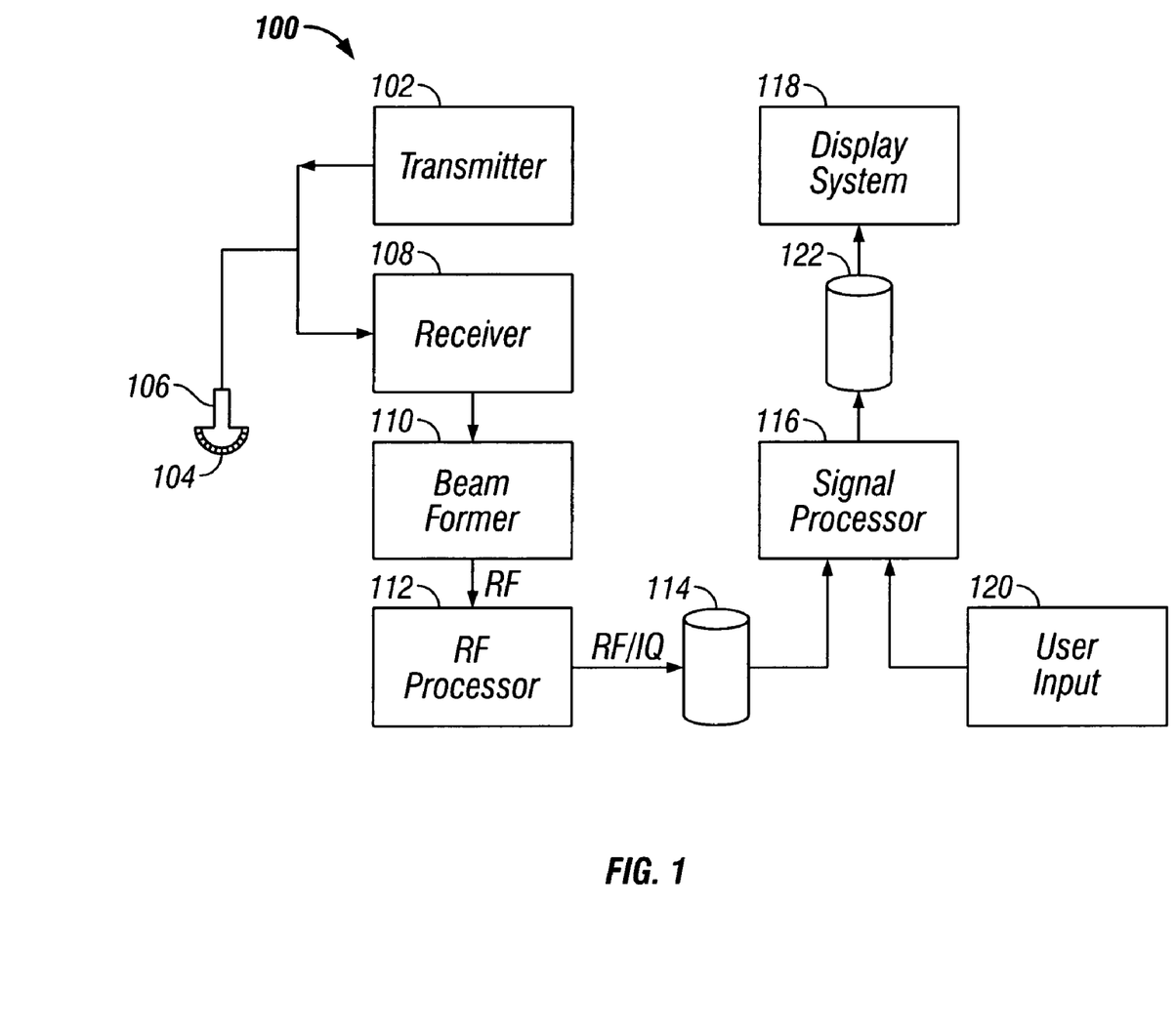
FIG. 1 illustrates a block diagram of an ultrasound system formed in accordance with an embodiment of the present invention.

FIG. 1 illustrates a block diagram of an ultrasound system 100 formed in accordance with an embodiment of the present invention. The ultrasound system 100 includes a transmitter 102 which drives elements 104 within a transducer 106 to emit pulsed ultrasonic signals into a body. A variety of geometries may be used. The ultrasonic signals are back-scattered from structures in the body, like blood cells or muscular tissue, to produce echoes which return to the elements 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to RF/IQ buffer 114 for temporary storage. A user input 120 may be used to input patient data, scan parameters, a change of scan mode, and the like.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in RF/IQ buffer 114 during a scanning session and processed in less than real-time in a live or off-line operation.

The ultrasound system 100 may continuously acquire ultrasound information at a frame rate that exceeds 50 frames per second—the approximate perception rate of the human eye. The acquired ultrasound information is displayed on the display system 118 at a slower frame-rate. An image buffer 122 is included for storing processed frames of acquired ultrasound information that are not scheduled to be displayed immediately. Preferably, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Figure 2:
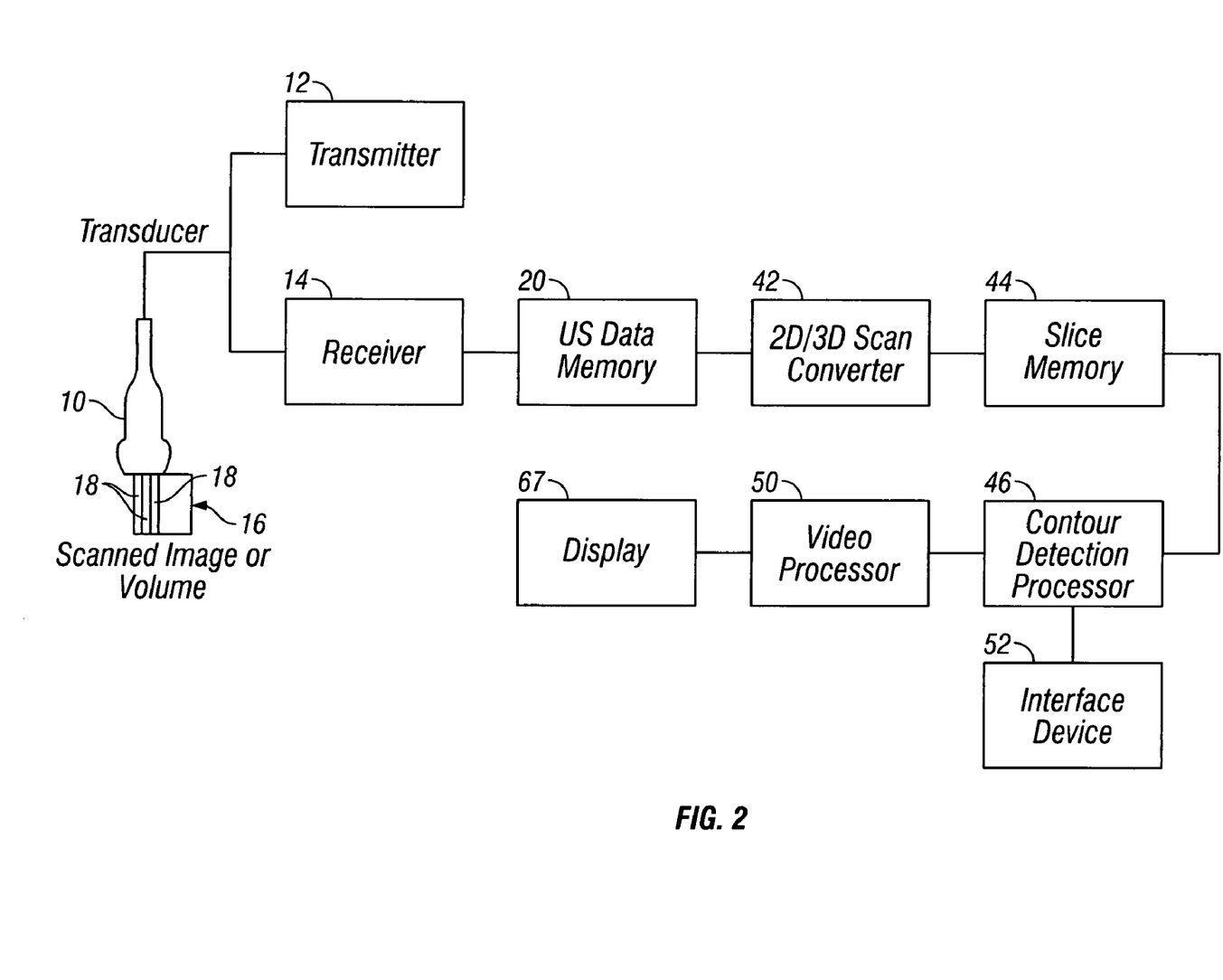
FIG. 2 illustrates an ultrasound system formed in accordance with an embodiment of the present invention.

FIG. 2 illustrates an ultrasound system formed in accordance with one embodiment of the present invention. The system includes a transducer 10 connected to a transmitter 12 and a receiver 14. The transducer 10 transmits ultrasonic pulses and receives echoes from structures inside of a scanned ultrasound image or volume 16. Memory 20 stores ultrasound data from the receiver 14 derived from the scanned ultrasound image or volume 16. The image or volume 16 may be obtained by various techniques (e.g., conventional B-mode scanning, 3D scanning, real-time 3D or 4D imaging, volume scanning, 2D scanning with an array of elements having positioning sensors, freehand scanning using a Voxel correlation technique, 2D or matrix array transducers and the like).

The transducer 10 is moved, such as along a linear or arcuate path, while scanning a region of interest (ROI). At each linear or arcuate position, the transducer 10 obtains 3D volume data or 2D scan planes 18. The volume data or scan planes 18 are stored in the memory 20, and then passed to a 2D/3D scan converter 42. In some embodiments, the transducer 10 may obtain lines instead of the scan planes 18, and the memory 20 may store lines obtained by the transducer 10 rather than the scan planes 18. The 2D/3D scan converter 42 creates a data slice from the volume data or from single or multiple 2D scan planes 18. The data slice is stored in slice memory 44 and is accessed by a contour detection processor 46. The contour detection processor 46 performs contour detection upon the data slice based upon input from one or more interface devices 52. The output of the contour detection processor 46 is passed to the video processor 50 and display 67.

The position of each echo signal sample (pixel for scanned image or Voxel for scanned volume) is defined in terms of geometrical accuracy (i.e., the distance from one pixel/Voxel to the next) and ultrasonic response (and derived values from the ultrasonic response). Suitable ultrasonic responses include gray scale values, color flow values, and angio or power Doppler information.

Figure 3:
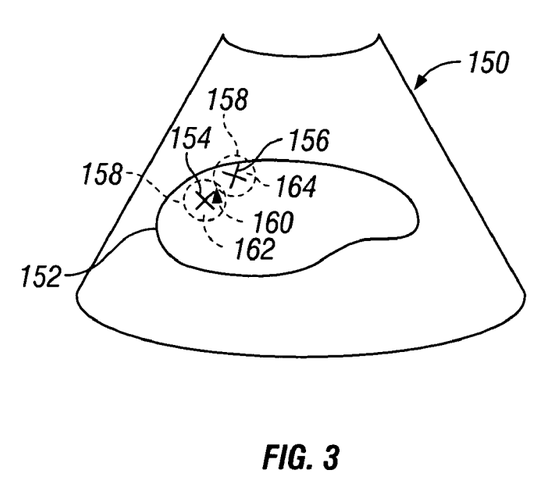
FIG. 3 illustrates selected points and associated outer ranges used to detect a contour of an object within an image in accordance with an embodiment of the present invention.

FIG. 3 illustrates an image 150 comprising diagnostic ultrasound data. It should be understood that although the below method and apparatus are discussed with respect to ultrasound, other diagnostic data may be used, such as, but not limited to, X-ray, MR and CT. The image 150 includes an object 152. By way of example only, the object 152 may be an organ, such as a liver or kidney, a tumor, cyst, blood vessel, and the like. The image 150 may comprise any diagnostic data, and may be based on a 2D, 3D, or 4D data set, for example.

To create a contour, or an outline, of the object 152, the user can select a first point 154 and a second point 156 within the object 152 with the interface device 52. The contour detection processor 46 uses one or more search algorithms capable of real-time processing which are known in the art. The contour detection processor 46 may use the search algorithm to define an outer range 158 around each of the first and second points 154 and 156. The outer ranges 158 define image subsets 162 and 164 around first and second points 154 and 156, respectively, which are the portions of the image 150 that the contour detection processor 46 will look within for an edge. The outer range 158 may be a predefined distance, or a preset limit, from the associated first and second points 154 and 156. In addition, the outer range 158 may define a volume around the associated first and second points 154 and 156, if the image comprises 3D or 4D data. In FIG. 3, the outer ranges 158 of the first and second points 154 and 156 overlap, creating a common area 160 of image data.

Alternatively, the contour detection processor 46 may not define an outer range 158, and instead search the image 150 closest to each of the first and second points 154 and 156 until an edge is detected. Once an edge is detected, the contour detection processor 46 may limit its search to be within a close proximity to the detected edge, until a completed edge encloses the first or second points 154 and 156.

Figure 4:
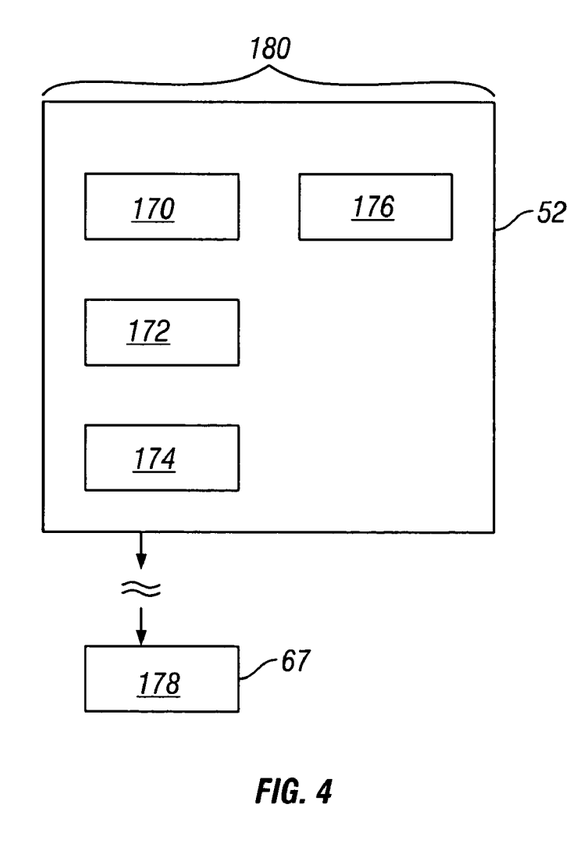
FIG. 4 illustrates the interface devices and display of FIG. 2 in accordance with an embodiment of the present invention.

FIG. 4 illustrates the interface device 52 and display 67 of FIG. 2. The interface device 52 may comprise one or more of a keyboard 170, mouse 172, track ball 174, and touch pad 176. The display 67 may also comprise a touch screen 178. The keyboard 170, mouse 172, track ball 174, touch pad 176 and touch screen 178 will be referred to collectively as interface devices 180. The user may use one or more of the interface devices 180 to interactively select points, areas and/or lines on the display 67.

Figure 5:
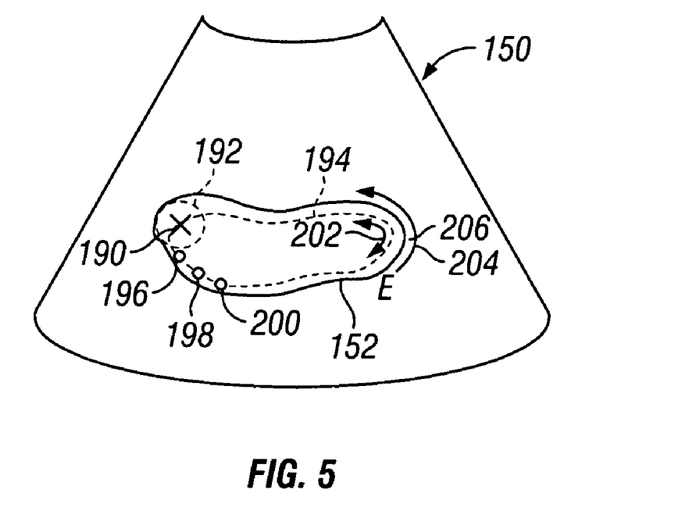
FIG. 5 illustrates a method of detecting the contour of an object within the image by drawing a line within the object in accordance with an embodiment of the present invention.

FIG. 5 illustrates a method of detecting a contour of the object 152 within the image 150 by drawing a line within the object 152. A point 190 has been defined by using one of the interface devices 180. The user then drags the pointer of the interface device 180 in an approximation path 194 around the edge of, and within, the object 152. The contour detection processor 46 may define an outer range 192 with respect to the point 190, and then define subsequent outer ranges around points automatically defined at predefined intervals along the approximation path 194, such as points 196-200. Alternatively, the contour detection processor 46 may define a search area 206 having an inner limit 202 and an outer limit 204 surrounding the approximation path 194, which are partially illustrated for clarity on FIG. 5. The search area 206 may be defined as a single search area having a predefined distance on each of the inner and outer sides with respect to the approximation path 194.

Figure 6:
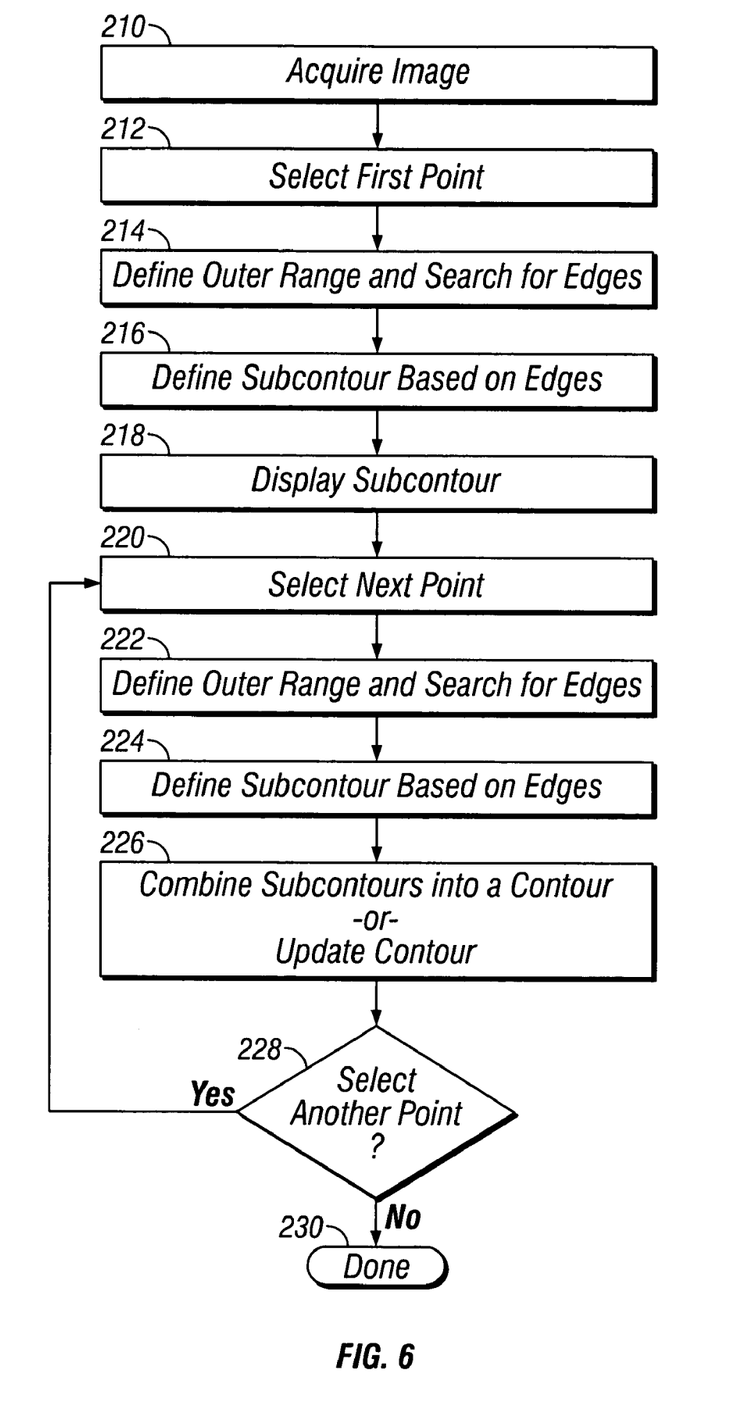
FIG. 6 illustrates a flow chart of a method for interactively using the user interface and/or interface devices to define the contour of an object in accordance with an embodiment of the present invention.

FIG. 6 illustrates a flow chart of a method for interactively using the interface device 52 and/or interface devices 180 to define the contour of an object, such as object 152. The method will be discussed with respect to FIGS. 1-5 and 7-9. In step 210, the ultrasound system 100 acquires an image 150 comprising an object 152. As discussed previously, the image 150 may comprise 2D, 3D, or 4D data. In step 212, the user selects the first point within the object 152, such as first point 154 or point 190.

In step 214, the contour detection processor 46 defines the outer range 158 (with respect to the first point 154) and searches the image subset 162 for edges. For example, the contour detection processor 46 may search the image subset 162 (FIG. 3) starting with image data closest to the first point 154 so that the closest edge is detected. An edge is detected where a change exists in the tissue. A change may be a difference in tissue densities, such as between tumor tissue and normal organ tissue, and different tissue types, such as between muscle and blood, or muscle and bone. Many variations exist within tissue, and therefore the contour detector processor 46 may or may not locate the edge of the object 152.

Turning to FIG. 5, the user may select the point 190 and drag the pointer of the interface device 180 along the approximation path 194. The contour detection processor 46 may identify N points at defined time intervals, such as a predefined number of times per second, or sample N points based on the speed of the contour detection algorithm. The contour detection processor 46 may search the search area 206 for an edge around a point N once all of the N points have been identified, or during the time between identifying each of the N points.

Figure 7:
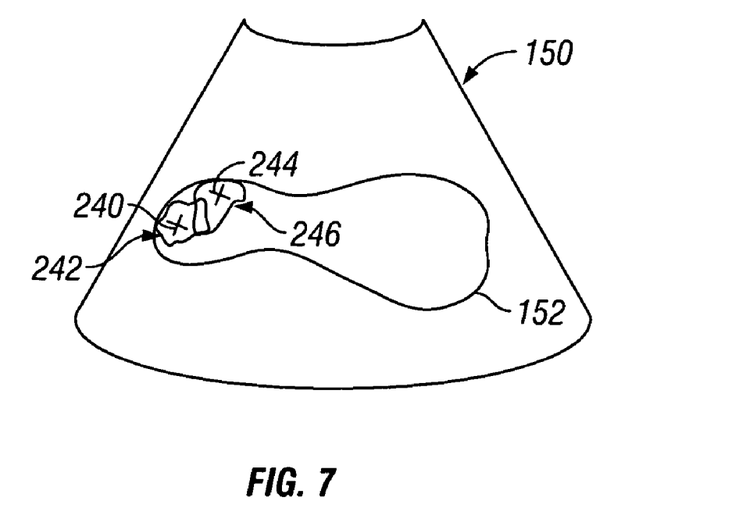
FIG. 7 illustrates first and second points having corresponding subcontours defined within the object in accordance with an embodiment of the present invention.

In step 216, the contour detection processor 46 defines a subcontour based on the detected edges, and in step 218, the display 118 displays the subcontour on the image 150. Turning to FIG. 7, FIG. 7 illustrates a first point 240 having a first subcontour 242. The first subcontour 242 follows the curves of the detected edges, and thus comprises an irregular shape and size. If a 3D image was being processed, the subcontour defined on the 3D image would comprise an irregularly shaped volume.

In step 220, the user selects a second point 244 (FIG. 7) within the object 152 with the interface devices 180. In step 222, the contour detection processor 46 defines an outer range with respect to the second point 244 and searches for edges within the outer range. It should be understood that the outer range defined for the second point 244 and N subsequent points may include data within the first subcontour 242 or the subcontour of one or more points within a close proximity.

In step 224, the contour detection processor 46 defines a second subcontour 246 based on the detected edges within the outer range defined around the second point 244. The first and second subcontours 242 and 246 may intersect or overlap.

In step 226, the contour detection processor 46 combines the first and second subcontours 242 and 246 into a contour. If a contour has already been identified around two or more points, the contour is updated. As discussed previously, if 3D images are acquired, the first and second subcontours may each comprise an irregularly shaped volume. The first and second volumetric subcontours would be combined into a single irregularly shaped volume. The contour would represent an outer edge surrounding the single irregularly shaped volume.

Figure 8:
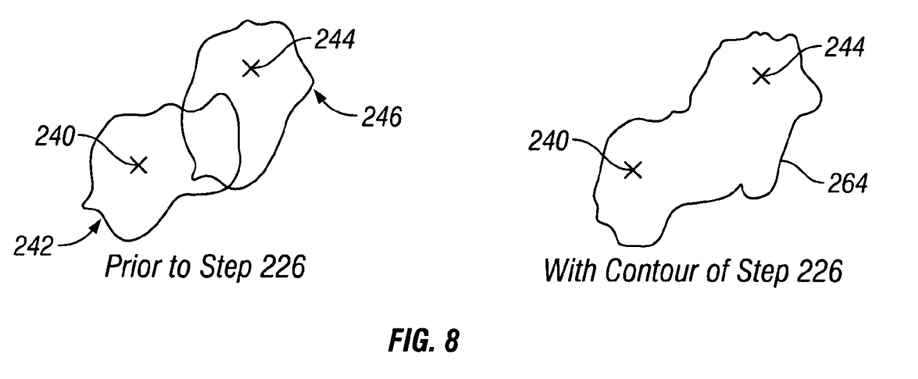
FIG. 8 illustrates first and second points having corresponding subcontours and a combined contour in accordance with an embodiment of the present invention.

FIG. 8 illustrates the first and second points 240 and 244, and first and second subcontours 242 and 246 of FIG. 7 prior to the combining step 226. Also illustrated are the first and second points 240 and 244 with a contour 264 as defined in step 226. The contour 264 follows the union of the outer edges of the first and second subcontours 242 and 246 and thus forms the single contour 264 around the first and second points 240 and 244.

Figure 9:
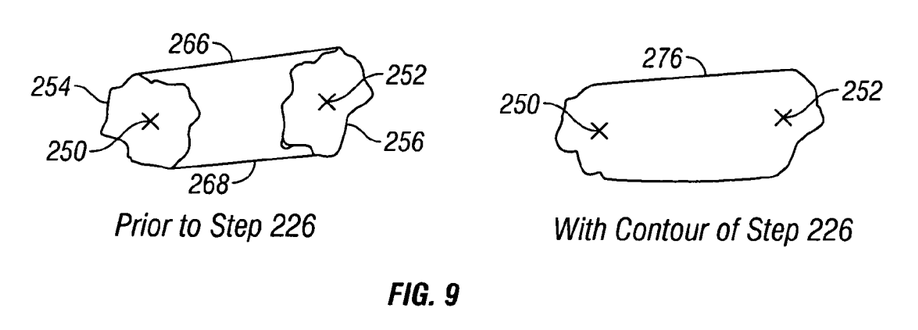
FIG. 9 illustrates first and second points having nonintersecting subcontours and a combined contour in accordance with an embodiment of the present invention.

FIG. 9 illustrates first and second points 250 and 252 having first and second subcontours 254 and 256, respectively, prior to the combining step 226. The first and second subcontours 254 and 256 do not intersect and represent two different regions of a 2D image. The contour detection processor 46 joins the first and second subcontours 254 and 256 by defining tangents or lines between the first and second subcontours 254 and 256. First and second tangents 266 and 268 may be defined on a top point and a bottom point of the first subcontour 254, respectively, and extend to a top point and a bottom point on the second subcontour 256. Therefore, a single contour 276 is defined in the combining step 226.

In step 228, the user may choose to select another point. If yes, the flow returns to step 220. If the user does not wish to select another point, the flow passes to step 230 and the method is complete.

Once the contour has been defined, the user may utilize the measurement package of the diagnostic system to calculate area, volume, circumference, object axis (such as long and/or short axis), and longest distance. For example, if the image acquired in step 210 is a 2D image comprising pixel data, the area within the contour may be calculated. If the image acquired in step 212 is a 3D image comprising Voxel data, the volume within the contour may be calculated.

Figures 10, 11:
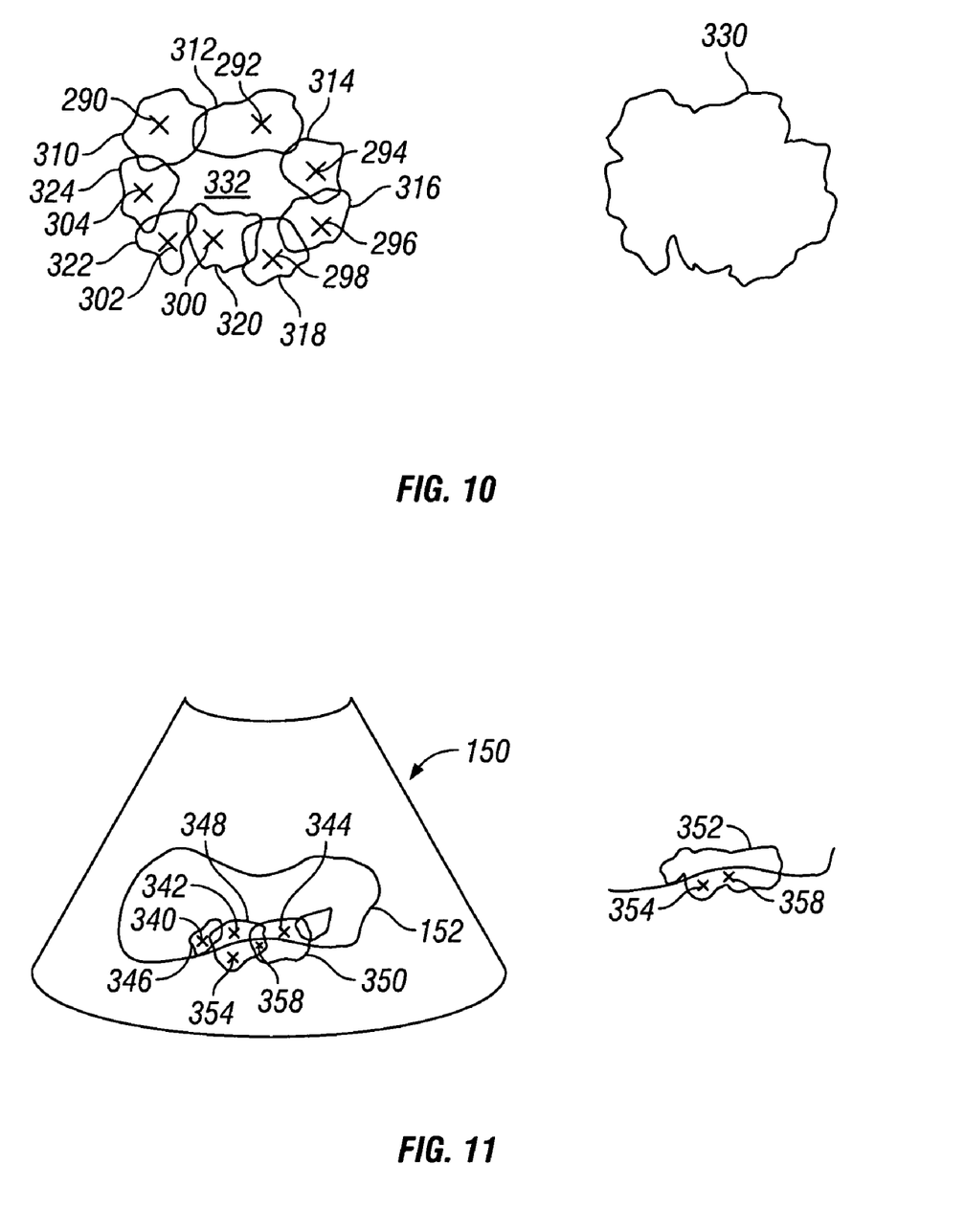
FIG. 10 illustrates subcontours forming a closed circle or loop around an interior portion and a combined contour in accordance with an embodiment of the present invention.
FIG. 11 illustrates a method of correcting a contour in accordance with an embodiment of the present invention.

FIG. 10 illustrates points 290-304, which have been selected by the user with the interface devices 180. The contour detection processor 46 has identified subcontours 310-324, corresponding to the points 290-304, respectively. The subcontours 310-324 form a closed circle or loop around an interior portion 332. In this example, the contour detection processor 46 calculates a single contour 330 (Step 226 of FIG. 6) which includes the interior portion 332.

FIG. 11 illustrates first, second, and third points 340, 342, and 344 having subcontours 346, 348, and 350, respectively. The subcontours 348 and 350 extend beyond the object 152. The contour detection processor 46 has joined the subcontours 346-350 to form contour 352.

The user may correct the contour 352 by selecting the desired area within the contour 352 with one of the interface devices 180. For example, the user may select an option, such as a button on the mouse 172, double click within the area, touch the touch screen at the desired location, and the like.

The contour detection processor 46 determines which subcontours include the selected point. For example, the user may use the interface device 52 to select point 354. Point 354 is located within subcontour 348 corresponding to the second point 342. The contour detection processor 46 deletes the second point 342 and recalculates the contour 352, such as by the tangent or line method as discussed with reference to FIG. 9. If a selected point is included in more than one subcontour, such as point 358 which is included in subcontours 348 and 350, the contour detection processor 46 deletes the second and third points 342 and 344 and recalculates the contour 352. The selecting and deleting of points may be done either during the method of FIG. 6, such as illustrated in FIG. 11, or after the entire contour has been calculated, such as illustrated in FIG. 10.

Figure 12:
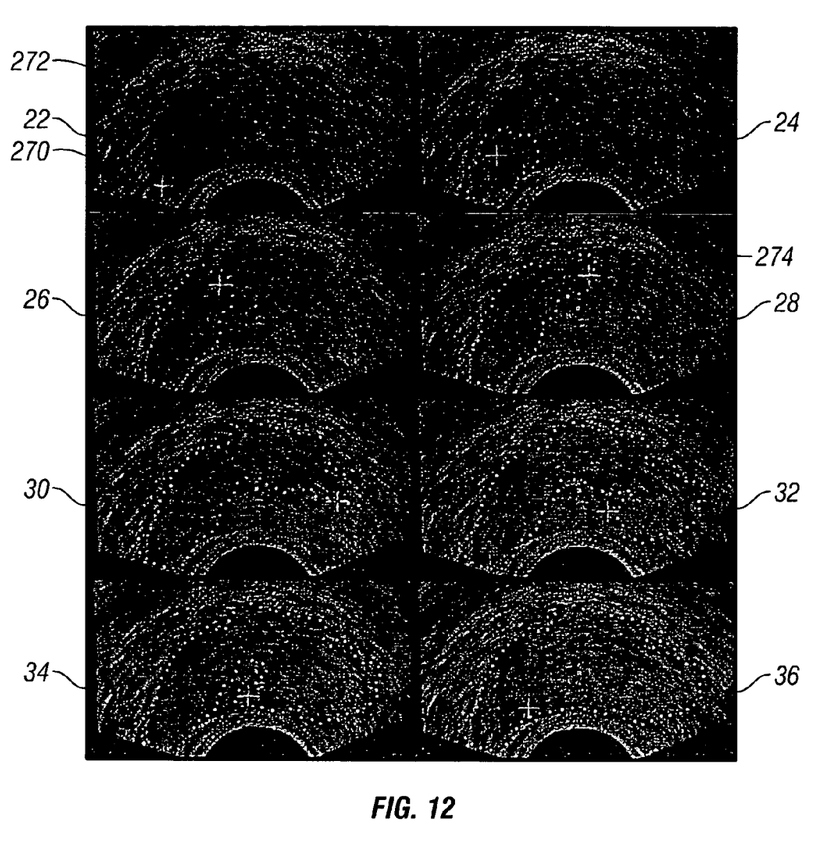
FIG. 12 illustrates a series of ultrasonic images displaying a method of defining a contour of an organ in accordance with an embodiment of the present invention.

FIG. 12 illustrates a series of ultrasonic images displaying the method of defining a contour of an organ. Image 22 illustrates a curser 270 moved to a location within an organ 272 by using one of the interface devices 180. By way of example only, the user may use the mouse 172 and select a starting point at the curser 270 location.

In image 24, the user has moved the curser 270 to a second location within the organ 272. The user may either select a second point, as previously discussed, or drag the cursor 270 close to the outer edge of the organ 272. A contour 274 is displayed on the display 118. The process is repeated for images 26 through 36, and the contour 274 is updated as the cursor 270 is dragged to new locations or additional points are selected.

Figure 13:
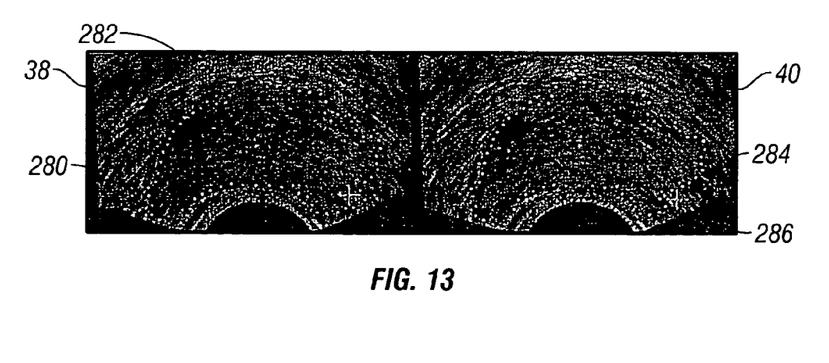
FIG. 13 illustrates two ultrasonic images displaying a correction of a contour in accordance with an embodiment of the present invention.

FIG. 13 illustrates two ultrasonic images displaying a correction of a contour. Image 38 illustrates a contour 280 defined around an organ 282. Image 40 illustrates an updated contour 284 after a delete operation has been performed by curser 286 as previously discussed with reference to FIG. 11.

While the invention has been described in terms of various specific embodiments, those skilled in the art will recognize that the invention can be practiced with modification within the spirit and scope of the claims.

What is claimed is:

1. An apparatus for detecting a contour of an object within an image, comprising:
    a user interface for selecting first and second points within an object, said object being within an image; and
    a processor for detecting first and second subcontours based on said first and second points, respectively, said first and second subcontours being based on detected edges, said processor combining said first and second subcontours into a contour and wherein a pre-set limit defines image subsets with respect to said first and second points, said processor searching said image subsets for said detected edges.

2. The method of claim 1, said user interface further comprising at least one of a mouse having at least one selectable button, a keyboard, a track ball, a touch screen, and a touch pad.

3. The method of claim 1, further comprising an ultrasonic transducer for transmitting and receiving ultrasonic information, said processor creating said contour in real-time.

4. The method of claim 1, said image being based on one of diagnostic ultrasonic, X-ray, CT, and MR data.

5. The method of claim 1, further comprising a display for displaying at least one of said first subcontour, said second subcontour, and said contour.

6. The method of claim 1, said user interface further comprising an input for deselecting a point within said contour, said processor defining an updated contour excluding said point.

7. The method of claim 1, further comprising a display for displaying said first subcontour after said processor detects said first subcontour, said display erasing said first subcontour and displaying said contour after said processor combines said first and second subcontours.

8. A user interactive method for detecting the contour of an object within an image; comprising:
    selecting a first point within an object using a user interface, said object being displayed within an image;
    identifying a first subcontour based on said first point;
    selecting a second point within said object using said user interface;
    identifying a second subcontour based on said second point; and
    defining a contour based on said first and second subcontours;
    selecting a third point using said user interface;
    defining a third subcontour based on said third point; and
    calculating an updated contour based on said contour and said third subcontour.

9. The method of claim 8, further comprising acquiring a diagnostic image comprising said object, said diagnostic image being one of ultrasonic, X-ray, CT and MR data and further comprising tissue data, said first and second subcontours being based on non-uniformities within said tissue data.

10. The method of claim 8, said first and second subcontours comprising nonintersecting image data with respect to each other, said method further comprising joining said first and second subcontours with first and second lines or tangents, said first and second lines or tangents being drawn based on top and bottom locations of said first and second subcontours, said contour being defined based on said first and second lines or tangents.

11. The method of claim 8, further comprising:
    drawing a line within said object by dragging a pointer with said user interface, said line beginning at said first point;
    defining outer and inner limits based on a pre-set limit with respect to said line, said outer and inner limits defining a search area; and
    searching said image within said search area for non-uniformities, said contour being based on said non-uniformities.

12. The method of claim 8, further comprising:
    displaying said first subcontour on a display;
    displaying said second subcontour on said display;
    erasing said first and second subcontours from said display after said defining step; and
    displaying said contour on said display.

13. The method of claim 8, further comprising:
    selecting a point within said contour using said user interface, said point identifying a pixel/Voxel to be deleted;
    identifying at least one subcontour including said point;
    deleting at least one point associated with said at least one subcontour; and
    updating said contour based on said contour and said point.

14. The method of claim 8, further comprising:
    selecting N points within said object using said user interface;
    identifying N subcontours based on said N points, said contour further comprising being defined based on N subcontours, said contour comprising a closed loop or circle around an interior portion; and
    updating said contour to include said interior portion.

15. A method for calculating and/or measuring parameters of an object within an image, comprising:
    acquiring an image comprising an object, said image further comprising pixel or Voxel data;
    selecting points within said object using a user interface;
    searching for edges within said image around said points as said points are selected, said edges being representative of non-uniformities in said pixel or Voxel data, said edges defining subcontours around each of said points;
    combining said subcontours into a contour as each of said subcontours is defined; and
    calculating a parameter within said contour, said parameter being at least one of area, volume, circumference, long axis, short axis, and longest distance.

16. The method of claim 15, further comprising:

selecting at least one additional point;

searching for said edges within said image around said at least one additional point, said edges defining said subcontour around said at least one additional point; and said combining step further comprising combining said subcontour and said contour to form an updated contour.

17. The method of claim 15, said image further comprising one of 2D and 3D tissue data.

18. The method of claim 15, further comprising:

said acquiring step further comprising acquiring a 3D volume of data;

said searching step further comprising searching for said edges around said points within said 3D volume, said subcontours forming irregularly shaped volumes based on said points; and said combining step further comprising combining said irregularly shaped volumes into said contour, said contour comprising a single irregularly shaped volume.

* * * * *